United States Patent [19]

Filhol et al.

[11] Patent Number: 5,547,995
[45] Date of Patent: Aug. 20, 1996

[54] USE OF SELEGILENE IN VETERINARY MEDICINE

[75] Inventors: Marie-Sophie Filhol, Talence; Thierny G. Pobel, Vayres, all of France

[73] Assignee: Sanofi Sante Nutrition Animale, Libourne, France

[21] Appl. No.: 235,965

[22] Filed: May 2, 1994

[30] Foreign Application Priority Data

May 4, 1993 [FR] France ................................. 93 05305
Dec. 22, 1993 [FR] France ................................. 93 15495

[51] Int. Cl.⁶ ................................................. A61K 31/135
[52] U.S. Cl. ............................................................ 514/654
[58] Field of Search ............................................. 514/654

[56] References Cited

U.S. PATENT DOCUMENTS 5,169,868  12/1992  Yu et al. ................................. 514/671
5,192,808  3/1993   Ruehl et al. ............................ 514/654

FOREIGN PATENT DOCUMENTS 0473252   3/1992   European Pat. Off. .
8804552   6/1988   WIPO .
9001928   3/1990   WIPO .
9118592  12/1991   WIPO .
9217169  10/1992   WIPO . .

OTHER PUBLICATIONS

Tariot et al., *Biological Abstracts*, vol. 84, No. 2, abstract #18676, 1987.

Goad et al, *Biological Abstracts*, vol. 92, No. 10, abstract #116325, 1991.

E. Head et al., "Changes in Spontaneous Behavior in the Dog Following Oral Administration of L–Deprenyl", Chemical Abstracts, vol. 117, No. 25, Dec. 21, 1992, Abstract No. 245502c.

*Primary Examiner*—Marianne M. Cintins
*Assistant Examiner*—William R. A. Jarvis
*Attorney, Agent, or Firm*—Jacobson, Price, Holman & Stern, PLLC

[57] ABSTRACT

The invention relates to the use of selegiline for preparing pharmaceutical compositions useful for treating behavioral disorders with change of mood in dogs and cats.

16 Claims, No Drawings

USE OF SELEGILENE IN VETERINARY MEDICINE present invention relates to the use of selegiline for the preparation of medicinal products useful for treating behavioral disorders with change of mood of pets, dogs and cats.

Selegiline, which is widely used in man in combination with levodopa in the treatment of parkinsonism, has also been studied in the treatment of diseases of ageing, such as Alzheimer's disease (cf. for example EP-A-0,406,488, -0,451,484).

It was recently described in EP-A-0,473,252 as being utilizable for retarding the damaging physiological effects of age on animals'bodies, in particular on the kidneys, the glands and the immune system and for limiting the deterioration of the learning and memorizing capacities of old cats and dogs; most of these activities, which can be observed only after a prolonged administration to the adult animals remain to be clinically demonstrated.

Other research scientists have observed in certain rats a substantial increase in life span when selegiline is regularly administered to them at the dose of 0.25 mg/kg after 23 months, whereas their average life span is 35 months; J. Knoll notes in Mechanisms of Ageing and Development 46 237-262 (1988) that this increase is accompanied by an improvement in the sexual activity of the animals and that these may be due to an action of selegiline on the dopaminergic neurons of the corpus striatum.

It has now been observed that the administration of selegiline to pets made it possible to improve very rapidly and to control in a few weeks their behaviour which is sometimes sufficiently intolerable for the owner to cause separation from his animal, euthanasia being frequently used at the present time.

Behavioral disorders with change of mood are characterized by a succession of phases of uncoordinated hyperactivity with insomnia, accompanied to a greater or lesser extent by aggressiveness and phases of apathy with difficulty in moving, by hypersomnia and hyporexia. Animals having such disorders are currently treated by administering to them neuroleptic drugs such as benzodiazepines or benzamides, whose efficacy, which appears only slowly, is often accompanied by a hypnotic activity.

Consequently, the invention relates to the use of selegiline, its racemate, the laevorotatory isomer or mixtures thereof in any proportions and pharmaceutically acceptable salts thereof for the preparation of a pharmaceutical composition for the treatment of behavioral disorders with change of mood in dogs and cats.

This composition may be provided in one of the pharmaceutical forms generally used in veterinary medicine, preferably for oral administration.

In this case, the daily dose of selegiline, HCl may range from 0.25 mg to 1 mg/kg of body weight of the animal and preferably close to 0.5 mg/kg; but these limits can be exceeded depending on the age of the animal or the intensity of the symptoms.

Since animals can be of very different weights, the medicinal product can be provided orally in a form which can be easily divided, for example in the form of divisible tablets, into 2 or 4 pieces, manually. It will be generally administered orally in the morning on an empty stomach.

The administration can be also performed subcutaneously, especially in cats, at the daily dose ranging from 0.25 to 4 mg/kg of selegiline, HCl.

The treatment will be preferably maintained for a few days after the disappearance of the symptoms, however, it seems to be unnecessary to prolong it beyond 8 weeks; in general, it will last for 3 to 6 weeks.

The pharmaceutical compositions conforming to the invention will be conventionally prepared with the excipients commonly used in the field in order to obtain solid, liquid or pasty compositions, especially tablets, hard gelatine capsules or powders; for example, tablets divisible into 4, containing 4 mg of selegiline, HCl per about 200 mg of excipient, will be recommended for animals of 2 to 8 kg whereas those comprising 10 mg of selegiline, HCl per 500 mg will be suitable for animals of 9 to 20 kg. For subcutaneous administration, aqueous solutions containing 10 mg of selegiline, HCl per ml will be used, the volume injected being from 0.5 to 2 ml according to the weight of the animal.

Reference can be made to manuals well known to galenists such as The theory and practice of Industrial Pharmacy—L. Lachman & al.—Lea & Febiger (1986)—Philadelphia, or Pharmacie galénique A. Denoël, Fr. Jaminet.—Presses Universitaire de Liège (1971).

1. Preliminary clinical study

In the following text, the clinical observations performed on dogs of various breeds, male or female, of more than 2 months old, whose behavioral disorders result in several symptoms in the following list are described:

bulimia with or without regurgitation and reingestion or, on the contrary, anorexia or dysorexia eudipsia, polydipsia or lapping water without drinking nibbling rituals or unusual licking urinary or faecal filthiness disrupted sleep The disturbed animal will steal items or will refuse to return them, will not respond to orders or to reprimand, will react badly, including with indifference, to changes and to oppressive situations.

In table I below are summarized the conclusions of the observations for dogs to which tablets containing 10 mg of selegiline had been administered daily, in the morning on an empty stomach at the indicated dose.

TABLE I

| Animal | Dose | Clinical Observations | Time required for cure |
| --- | --- | --- | --- |
| Dog No. | 0.5 mg/kg | An improvement in visible from the first dose | Cure in 21 days |
| Dog No. 2 | 0.5 mg/kg | An improvement in visible from the first dose | Cure in 21 days |
| Dog No. 3 | 0.5 mg/kg | An improvement is visible from the first dose | Cure in 60 days |
| Dog No. 4 | 0.5 mg/kg | Improvement after one week | Care in 60 days |
| Dog No. 5 | 0.25 mg/kg | The modifications are not very visible, the filthiness in not halted, no side effects | Improvement without cure |
| Dog No. 6 | 0.25 mg/kg | The modifications are not very visible, the filthiness in not halted, no side effects | Improvement without cure |

From the clinical point of view, we observed disorders dominated by the production of disproportionate, frequent and prolonged emotional responses. These manifestations tend, in the case of those which have a voluntary expression to become uncontrolled and to progress to stereotypies. Thus, licking activities are observed, gradually losing their spontaneous interruption and result in a stereotyped licking which gradually invades the periods of wakefulness. The same applies to bulimias and potomanias, but includes aggressive responses with emotional components and the like. Sleep disorders corresponding to an advancing of paradoxical sleep resulting in sudden waking during the first 90 minutes of sleep and associated with phases of anxiety and agitation as bedtime approaches, are systematically observed in these animals. This precise typology led us to define a numerical scale for evaluation of the thymic state of the animals which we will call EEDD (Evaluation of the Emotional Disorders of Dogs) which will serve us as a tool for monitoring the treated animals and will permit a quantification of their cure.

EEDD ≦ 20 normal animal

EEDD > 20 animal suffering from behavioral disorders with change of mood.

The evaluation scale appended to the specification.

2. Clinical study

In Table II below are summarized the results of a study performed on 25 various pedigree dogs. The EEDD value was measured on the first day (D=0), 30th day (D=30) and 60 th day (D=60) of the treatment.

| dysthymia | intermittent anxiety |
| involution depression | paroxystic anxiety |
| aggressiveness via dominance | instrumental sociopathy |
| hyperactivity | stereotypy (staggers/leaking) |
| deprivation syndrome | phobia (human/urban) |
| separation anxiety | socialization disorders |

TABLE II

| ANIMAL | | EEDD | | | |
| --- | --- | --- | --- | --- | --- |
| Name or Breed | Age | D = 0 | D = 30 | D = 60 | DIAGNOSIS |
| Black Poodle | 17 yrs | 42 | 15 | 11 | Dysthymia |
| Irish Setter | 05 yrs | 40 | 14 | 11 | Dysthymia |
| Pinscher Crossbreed | 06 yrs | 37 | 22 | 20 | Dysthymia |
| Poodle | 07 yrs | 26 | 14 | 14 | Dysthymia |
| Alsatian | 08 yrs | 36 | 16 | 15 | Involution depression |
| Cocker Spaniel | 12 yrs | 43 | 23 | 18 | Aggressive, dominant |
| Sheepdog Crossbreed | 2.5 yrs | 39 | 23 | — | Dominant + nibbling stereotypy |
| Dark | 0.5 yrs | 24 | 24 | 13 | Hyperactivity + intermittent anxiety |
| Pinscher | 01 yr | 38 | 21 | 19 | Hyperactivity + hyperattachment |
| Labrador | 10 mths | 44 | 18 | 14 | Hyperactivity |
| Pyrenean Sheepdog | 03 yrs | 43 | 19 | 18 | Deprivation syndrome |
| Virgil | 08 yrs | 22 | 19 | 19 | Separation anxiety |
| Christopher | 06 yrs | 25 | 18 | — | Separation anxiety |
| Hatoll | 01 yr | 26 | 18 | 13 | Separation anxiety |
| Libre | 06 yrs | 26 | 20 | 19 | Overall anxiety |
| Elia | 4.5 yrs | 25 | 25 | 10 | Overall anxiety |
| Honorine | 1.5 yrs | 22 | 21 | 15 | Overall anxiety |
| Scarlett | 05 yrs | 21 | 22 | 15 | Paroxystic anxiety |
| Pyrenean Mountain dog | 05 yrs | 30 | 24 | 18 | Polyphobia - staggers stereotypy |
| Leonberg | 10 mths | 24 | 21 | 18 | Polyphobia + permanent anxiety |
| Alsatian | 03 yrs | 22 | 22 | 15 | Human phobia |
| Alsatian | 02 yrs | 24 | 20 | | Urban phobia + sociopathy |
| Doberman | 01 yr | 22 | 17 | 16 | Urban phobia + intermittent anxiety |
| Sheepdog Crossbreed | 05 yrs | 30 | 32 | 17 | Instrumental sociopathy |
| Poodle | 10 yrs | 29 | 22 | | Instrumental sociopathy + staggers |

This study demonstrates the effectiveness of the use of selegiline according to the present invention. The animals, practically without exception, reached, at the end of the treatment, an EEDD of less than 20, which characterizes a normal state.

Consequently, selegiline can be used in behavioral disorders with change of mood covering the following pathologies:

| BEHAVIOUR | ITEM | | NOTE |
|---|---|---|---|
| CENTRIPENTAL | Eating | Bulimia | 3 |
| | | Anorexia/hyporexia | 4 |
| | | Dysorexia (passage from hyper to hypo) | 5 |
| | | Normal appetite | 1 |
| | | Bulimia with regurgitation and reingestion | 3 |
| | Drinking | Eudipsia | 1 |
| | | Polydipsia (documented) | 5 |
| | | Lapping water without drinking | 3 |
| | | Playing with the empty bowl | 2 |
| | Habits | Normal hygiene pattern | 1 |
| | | Licking, nibbling | 4 |
| | | Nibbling stereotypy, staggers | 5 |
| | Sleep pattern | Normal (or no change) | 1 |
| | | Increase, hypersomnia | 2 |
| | | Insomnia during sleep | 3 |
| | | Wakes shortly after going to bed, sleep anxiety | 5 |
| CENTRIFUGAL | Inquisitiveness | Normal | 1 |
| | | Simply inhibited | 2 |
| | | Increased and hypervigilance | 4 |
| | | Oral | 5 |
| | | Hides often | 3 |
| | Aggression | Unchanged agressiveness (no relationship problems) | 1 |
| | | Aggression from irritation | 3 |
| | | Aggression from fear | 4 |
| | | Aggression from fear and from irritation | 5 |
| | Social Relationships | Steals, does not release the stolen items | 5 |
| | | Bites without growling | 4 |
| | | Not submissive | 2 |
| | | No self-control during play | 2 |
| | | Unchanged | 1 |
| | Specific Relationships | Same response capacity (taking fatigability into account) | 1 |
| | | Unpredictable response | 3 |
| | | No further response | 5 |
| | Physical condition | Normal | 1 |
| | | Episodic tachycardia and/or tachypnoea | 2 |
| | | Diarrhoea, colic | 2 |
| | | Dyspepsia | 2 |
| | | Increased urination | 3 |
| | | Lick granuloma | 4 |
| | | Obesity | 4 |
| | | P.U.P.D. (poly urea/poly dypsia | 4 |
| | | TOTAL | |

We claim:

1. A method for the treatment of a behavioral disorder with change of mood comprising administering to a mammal in need thereof selected from dogs and cats, an active ingredient selected from selegiline, its racemate, the laevorotatory isomer, mixtures thereof in any proportions and pharmaceutically acceptable salts thereof, in association with a pharmaceutically acceptable carrier.

2. The method of claim 1, wherein the active ingredient is selegiline HCl, the daily doses for oral administration ranging from 0.25 to 1 mg of selegiline, HCl per kg of body weight of the animal.

3. The method of claim 1, wherein the active ingredient is selegiline HCl, the daily doses for subcutaenous administration ranging from 0.25 to 4 mg of selegiline, HCl per kg of body weight of the animal.

4. The method of claim 1 wherein the behavioral disorder is dysthymia.

5. The method of claim 1 wherein the behavioral disorder is involution depression.

6. The method of claim 1 wherein the behavioral disorder is aggressiveness via dominance.

7. The method of claim 1 wherein the behavioral disorder is hyperactivity.

8. The method of claim 1 wherein the behavioral disorder is deprivation syndrome.

9. The method of claim 1 wherein the behavioral disorder is separation anxiety.

10. The method of claim 1 wherein the behavioral disorder is intermittent anxiety.

11. The method of claim 1 wherein the behavioral disorder is paroxystic anxiety.

12. The method of claim 1 wherein the behavioral disorder is instrumental sociopathy.

13. The method of claim 1 wherein the behavioral disorder is stereotypies.

14. The method of claim 1 wherein the behavioral disorder is phobia.

15. The method of claim 1 wherein the behavioral disorder is socialization disorders.

16. A method for the treatment of behavioral disorders with change of mood, said behavioral disorders being selected from dysthymia, involution depression, aggressiveness via dominance, hyperactivity, deprivation syndrome, separation anxiety, intermittent anxiety, paroxystic anxiety, instrumental sociopathy, stereotypies, phobia and socialization disorders, comprising administering to a mammal in need thereof selected from dogs and cats, an active ingredient selected from selegiline, its racemate, the laevorotatory isomer, mixtures thereof in any proportions and pharmaceutically acceptable salts thereof, in association with a pharmaceutically acceptable carrier.

* * * * *

US005547995B1

REEXAMINATION CERTIFICATE (3431th)

United States Patent [19]
Filhol et al.

[11] B1 5,547,995
[45] Certificate Issued Jan. 27, 1998

[54] USE OF SELEGILINE IN VETERINARY MEDICINE

[75] Inventors: Marie-Sophie Filhol, Talence; Thierny G. Pobel, Vayres, both of France

[73] Assignee: Sanofi Sante Nutrition Animale, Libourne, France

Reexamination Request:
No. 90/004,502, Dec. 26, 1996

Reexamination Certificate for:
Patent No.: 5,547,995
Issued: Aug. 20, 1996
Appl. No.: 235,965
Filed: May 2, 1994

[30] Foreign Application Priority Data

May 4, 1993 [FR] France .................................. 93 05305
Dec. 22, 1993 [FR] France .................................. 93 15495

[51] Int. Cl.$^6$ .................................................. A61K 31/135
[52] U.S. Cl. .................................................. 514/654
[58] Field of Search .................................................. 514/654

[56] References Cited

U.S. PATENT DOCUMENTS

5,151,449   9/1992   Milgram .................................. 514/654

OTHER PUBLICATIONS

*American Veterinary Society of Animal Behavior*, Apr. 1993, vol. 15, No. 1.
*Veterinary Product News*, Jul./Aug. 1993, vol. 5, No. 5.

*Primary Examiner*—William R. A. Jarvis

[57] ABSTRACT

The invention relates to the use of selegiline for preparing pharmaceutical compositions useful for treating behavioral disorders with change of mood in dogs and cats.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–16 is confirmed.

\* \* \* \* \*